(12) United States Patent
Huang et al.

(10) Patent No.: US 8,178,486 B2
(45) Date of Patent: May 15, 2012

(54) METHOD FOR PROMOTING HAIR GROWTH

(75) Inventors: Hsiu-Chin Huang, Jhubei (TW);
Min-Chuan Huang, Jhubei (TW);
Pei-Chun Chen, Chungli (TW);
Chung-Nan Weng, Chunan Town (TW)

(73) Assignee: Animal Technology Institute Taiwan, Miaoli County (TW)

( * ) Notice: Subject to any disclaimer, the term of this patent is extended or adjusted under 35 U.S.C. 154(b) by 445 days.

(21) Appl. No.: 11/187,394

(22) Filed: Jul. 21, 2005

(65) Prior Publication Data
US 2007/0020219 A1 Jan. 25, 2007

(51) Int. Cl.
*C07K 14/00* (2006.01)

(52) U.S. Cl. .......................................... 514/1
(58) Field of Classification Search ............ 514/2
See application file for complete search history.

(56) References Cited

U.S. PATENT DOCUMENTS

2003/0190303 A1* 10/2003 Kimber et al. ............ 424/78.05

FOREIGN PATENT DOCUMENTS

| JP | 07-196529 | * | 8/1995 |
| WO | WO 0146254 A1 | * | 6/2001 |
| WO | WO 2004014413 A1 | * | 2/2004 |

OTHER PUBLICATIONS

P. C. Arck et al., "Topical minoxidil counteracts stress-induced hair growth inhibition in mice," Experimental Dermatology, 12:580-590 (2003) (Blackwell Munksgaard, Printed in Denmark).

Saood Murad et al., "Suppression of Fibroblast Proliferation and Lysyl Hydroxylase Activity by Minoxidil," The Journal of Biological Chemistry, 262(25):11973-11978, Issue of Sep. 5, (1978).

G. P. Moore et al., "Epidermal hyperplasia and wool follicle regression in sheep infused with epidermal growth factor," J. Invest. Dermatol., 84(3):172-175 (Mar. 1985), Abstract Only.

G. P. Moore et al., "Inhibition of wool growth in merino sheep following administration of mouse epidermal growth factor and a derivative," Aust. J. Biol. Sci., 35(2):163-172 (1982), Abstract Only.

G. P. Moore et al., "Effects of epidermal growth factor on hair growth in the mouse," 88(2):293-299 (1981), Abstract Only.

* cited by examiner

*Primary Examiner* — Karen Carlson
(74) *Attorney, Agent, or Firm* — Occhiuti Rohlicek & Tsao LLP

(57) ABSTRACT

A method is provided of promoting hair growth in a subject includes applying to the skin of the subject a composition including lactoferrin in an amount effective for at least one of proliferating and activating hair follicles in the hypodermis of skin of the subject.

11 Claims, 6 Drawing Sheets

METHOD FOR PROMOTING HAIR GROWTH

BACKGROUND OF THE INVENTION

The present invention is generally related to a method of promoting hair growth, and more particularly related to a novel use of lactoferrin for promoting hair growth.

Lactoferrin, a 78-80 kDa glycoprotein (Nuijens, 1996), is mainly distributed in a body fluid, such as breast milk, saliva, tear drop and mucosal secretion of a mammalian animal, and it may be released as a result of an inflammation reaction by an activated neutrophil. Physiologically, lactoferrin plays several regulatory roles in human and animal functions. For example, lactoferrin at certain concentration may effectively inhibit growth of *Escherichia coli, Streptococcus, Neisseria* and other bacteria, promote differentiation of lymphatic cells, and regulate proliferation of macrophages and granulocytes. In the gastrointestinal tract, lactoferrin functions in transportation and absorption of ferric ions. According to recent research reports, lactoferrin was found to inhibit tumor cell proliferation and metastasis, and was even used to combat against Enterovirus-related disease, Severe Acute Respiratory Syndrome (SARS) and hepatitis C.

It was disclosed in one Japanese patent (JP8040824) that a variety of cosmetics were made from lactoferrin for improving skin roughness, wherein the lactoferrin removed ferric ions from bacteria to exhibit an antibacterial effect. According to disclosure of another Japanese patent (JP5065214), lactoferrin was used in a composition for protecting hair from mechanical deterioration, whereby mechanical properties of hair, especially its tensile resistance and elasticity were protected from damage due to exposure to air and light. However, none of the prior art disclosures teaches or suggests the use of lactoferrin to promote hair growth.

Typical methods of inducing hair growth focus on manipulating cell death to prevent premature baldness or graying of hair. Despite the vigorous research and development focusing on hair growth agents, the hair fostering action, namely hair loss prevention and hair growth effects and the like, of conventional hair growth agents has not always been adequate. A number of hair growth stimuli were developed from growth factors, hormones, plant extracts, and a combination thereof with limited success achieved so far.

Currently available treatments acknowledged by dermatologists include orally administered PROPECIA® and externally applied Rogaine® (Messenger AG, Rundegren J. Minoxidil: mechanisms of action on hair growth. Br J Dermatol. 2004 February; 150(2): 186-94. Review). PROPECIA® is the first and only FDA-approved pill demonstrated to treat male pattern hair loss on the vertex (top of head) and anterior mid-scalp area (middle front of head) in men. However, it is not effective when used by females and may have a side effect of impairing male sexual function. Rogaine® has been known as minoxidil and used topically to stimulate hair growth on the bald spot of the back of the head in men. In women, Rogaine® can increase hair growth in the forehead areas. Yet, an increase in the absorption of minoxidil from the scalp can occur in patients with inflamed or abnormal scalps, leading to side effects, including a fall in blood pressure, an increase in the heart rate, and weight gain (fluid retention). As a result, Rogaine® is usually used with caution in those with high blood pressure. Also, the alcohol base in Rogaine® can irritate the eyes.

There is a long-felt and still growing need for a method of promoting hair growth in humans using a hair growth-promoting agent free of the side effects mentioned above. The present invention satisfies that need.

BRIEF SUMMARY OF THE INVENTION

One aspect of the present invention provides a method of promoting hair growth in a subject comprising applying to the skin of the subject a composition comprising lactoferrin in an amount effective for at least one of proliferating and activating hair follicles in hypodermis of skin of the subject.

Further in accordance with the present invention, there is provided a novel use of lactoferrin for promoting hair growth in a subject.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Figure 1A:
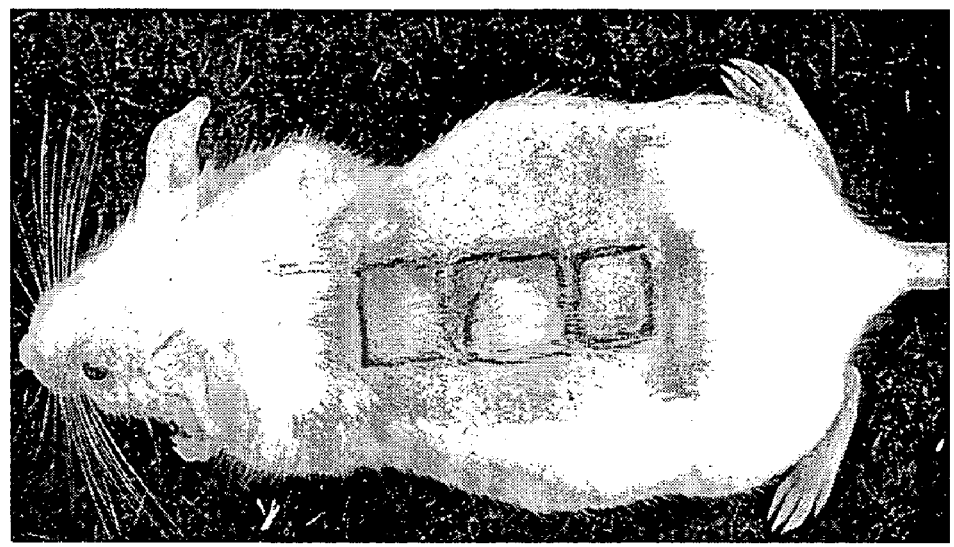
FIG. 1A is a macroscopic image showing a top view of a 2-month old ICR mouse with a patch of shaved dorsal skin, and the skin is further marked with three treatment areas.

For a better understanding of the present invention, some of the terms used herein are explained in more detail.

As used herein, the article "a" or "an" means one or more than one (that is, at least one) of the grammatical object of the article, unless otherwise made clear in the specific use of the article in only a singular sense.

The term "hair follicle" as used herein refers to a hair structure underneath the skin with a stocking-like structure that contains several layers with different functions. Each hair passes through three distinct phases, namely anagen, catagen and telogen between starting to grow and falling out years later. The "anagen" phase is the active growth phase of hair follicles. The cells in the root of the hair are dividing rapidly, adding to the hair shaft. The "catagen" phase refers to a short transition phase that occurs at the end of the anagen phase. It signals the end of the active growth of a hair. The "telogen" phase is the resting phase of the hair follicle. During this phase the hair follicle is completely at rest and the club hair (where the hair root is surrounded by a bulbous enlargement composed of completely keratinized cells) is completely formed.

The present invention provides a method of promoting hair growth in a subject comprising applying to the skin of the subject a composition comprising lactoferrin in an amount effective for at least one of proliferating and activating hair follicles in hypodermis of skin of the subject. The term "subject" as used herein refers to a human or an animal with hair, preferably a warm-blooded animal which includes mammals that have hair follicles or hair follicle epithelial cells, and birds.

An amount is "effective" as used herein, when the amount provides an effect in promoting hair growth in the subject. For those skilled in the art, the effective amount, as well as dosage and frequency of administration, may easily be determined according to their knowledge and standard methodology of merely routine experimentation based on the present disclosure.

As used herein, "lactoferrin" includes bovine lactoferrin, rabbit lactoferrin, human lactoferrin, lactoferrin extracted from other animal species, lactoferrin derived synthetically, and derivatives of any of the foregoing types of lactoferrin, such as lactoferricin, which also provide beneficial hair growth promotion properties. In a preferred embodiment of the invention, the lactoferrin in the composition includes bovine lactoferrin, which is readily available commercially, such as from Sigma Chemical Company, St. Louis, Mo., U.S.A.

It was found in the invention that an increased number of the hair follicles were activated to re-enter the anagen phase, where the hair follicles were highly active metabolically, with a thickening of the hypodermis and the hair rapidly grew on the lactoferrin-treated skin. According to the invention, lactoferrin was found to be effective in the promotion of hair growth regardless of the subject's gender or age, and the hair grew much faster and in greater volume and amount on the treated animals than those animals without the lactoferrin treatment.

The composition comprising lactoferrin may be applied to the skin of a subject through any method known in the field, including but not limited to topically spreading, spraying, steaming, or injecting the composition comprising lactoferrin onto or into the skin where hair growth promotion is desired. Alternatively, the subjects having the hair growth problem may be soaked or bathed in the composition comprising lactoferrin. According to the invention, the amount of lactoferrin in the composition may be about 50 mg/ml to about 500 mg/ml, preferably about 100 mg/ml to about 250 mg/ml, and more preferably, about 200 mg/ml.

The composition comprising lactoferrin may be made by mixing lactoferrin with other active or inactive ingredients, into a variety of forms for convenient use. Such other ingredients may include, by way of non-limiting examples, an adjuvant, vehicle or excipient, perfume, colorant, stabilizer or any other inactive ingredient, or any combination of them, with or without other active ingredients. Preferred inactive ingredients include, for example without limitation dimethyl sulfoxide (DMSO), glycerol, collagen, and hyluronan (HA). For example without limitation, the composition may be formulated in the form of an ointment, shampoo, conditioner, lotion, tonic, gel or mousse. The composition of the present invention may contain various additional active components and supplementary components normally used in topical formulations in an amount that does not adversely influence the hair growth promoting effect of lactoferrin, such as growth factors, hormones, and cell proliferating factors known by those skilled in the pertinent art.

Suitable dosages of the lactoferrin active ingredient, as previously defined herein, may be determined readily without undue experimentation in view of the present disclosure. Suitable dosages of the lactoferrin active ingredient may be, for example without limitation, about 1 mg or less to about 20 or more mg of lactoferrin, preferably about 3 mg to about 15 mg lactoferrin, and more preferably about 6 mg to about 12 mg lactoferrin. The lactoferrin composition may be applied once daily when convenient, twice daily preferably in the morning an evening, or more than twice daily depending on the individual need of the subject for promoting hair growth.

The present invention also provides a novel use of lactoferrin for promoting hair growth in an animal.

The invention will now be described in further detail with reference to the following specific, non-limiting examples.

Example 1

Effect of Lactoferrin in Increasing Hair Growth in Young Mice

Figure 1B:
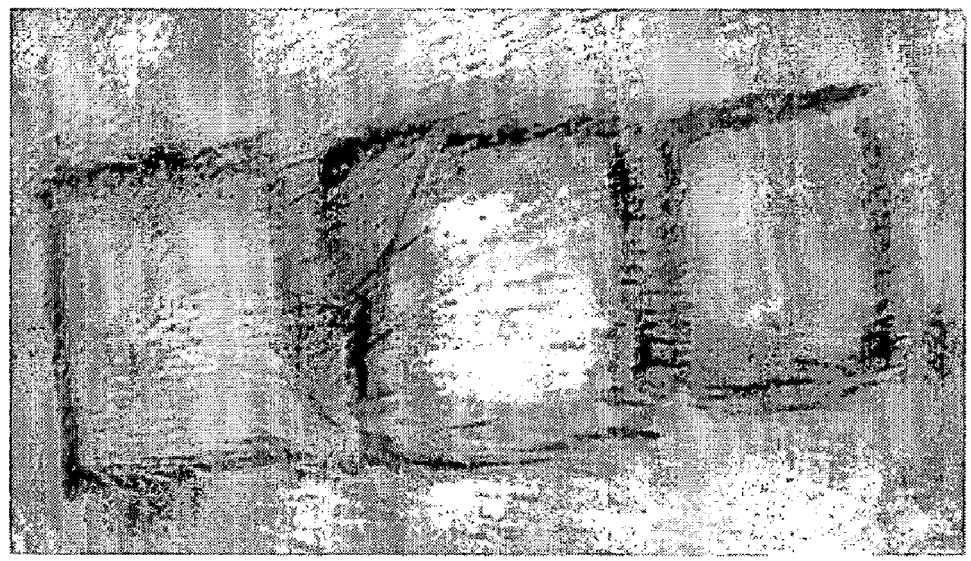
FIG. 1B is an image of a magnified view of the three treatment areas as marked in FIG. 1A.

To study the effect of lactoferrin in hair growth in young mice, five male ICR (outbred) mice, each 2 months old, were shaved to expose a portion of dorsal skin. For each treated mouse, the exposed portion of dorsal skin was further marked with three areas as illustrated in FIG. 1A to be subsequently administered different treatments. Referring to FIG. 1B, the three marked areas (from left to right) were treated by spreading topically on the exposed skin areas 60 µl of bovine lactoferrin (as an aqueous solution of 100 mg/ml), 60 µl of bovine lactoferrin (of 200 mg/ml) and 60 µl of control vehicle (water), respectively, on a twice daily basis. Observation for hair growth in the marked areas was made daily after the first treatment. As shown in FIGS. 1A and 1B, more rapid hair growth was observed in the lactoferrin-treated skin than in the control vehicle-treated skin. The hair growth was observed on all five mice administered 200 mg/ml of lactoferrin 2 to 4 days after the treatment. The mice administered 100 mg/ml of lactoferrin were found to have their hair growth 3 to 5 days after the treatment. In contrast, the skin exposed with the control vehicle (water) alone exhibited hair growth only 15-17 days after the treatment.

Figure 2A:
FIG. 2A is a microscopic image showing a histological slide of the skin tissue from the 2-month old ICR mouse treated with a control vehicle (water), the image having a 100× magnification with a scale bar of 100 μm.
Figure 2B:
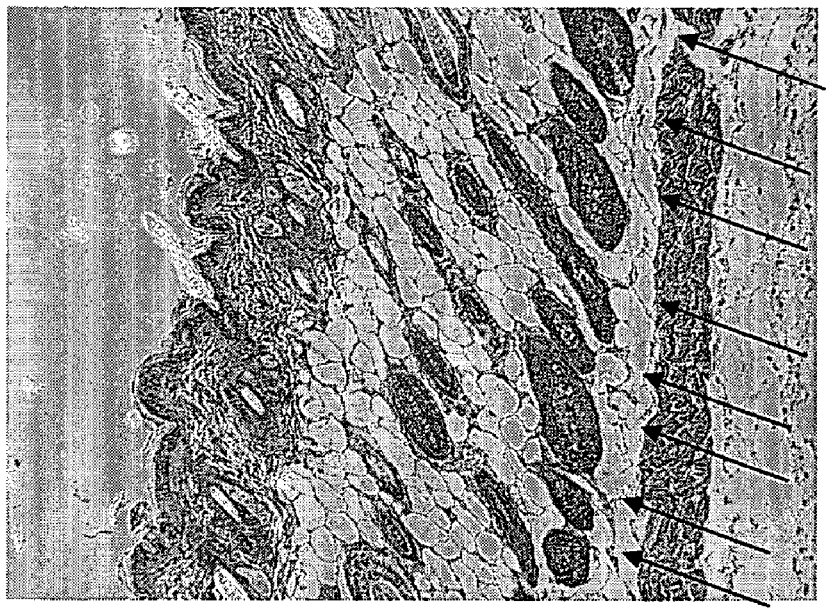
FIG. 2B is a microscopic image showing a histological slide of the skin tissue from the same 2-month old ICR mouse shown in FIG. 2A treated with lactoferrin, the image having the same magnification as FIG. 2A.
Figure 3A:
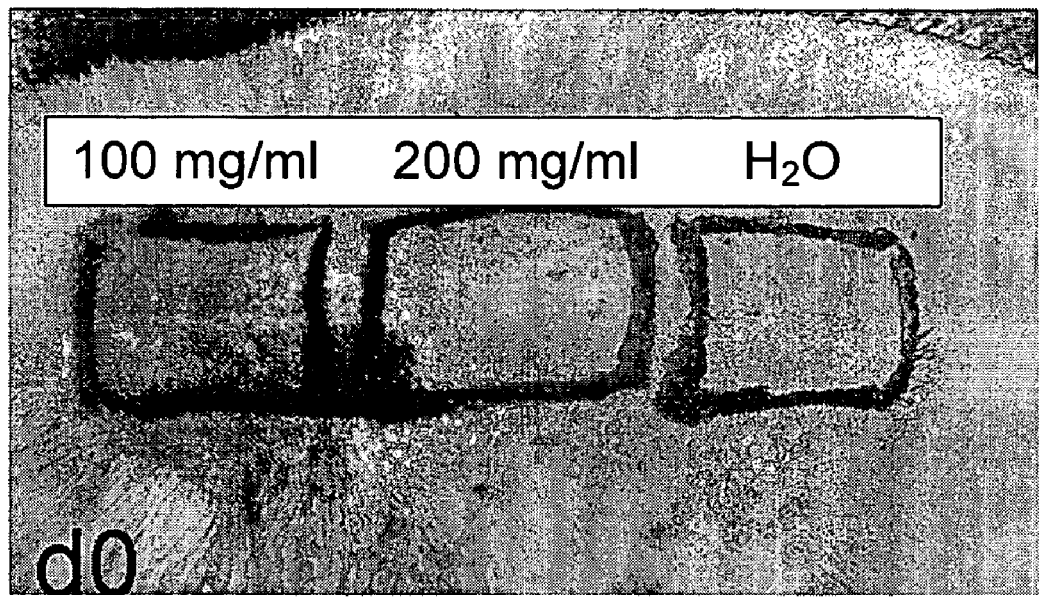
FIGS. 3A through 3D are macroscopic images showing progressive hair growth at the three treatment areas of an 11-month old mouse on day 0 (d0), day 3 (d3), day 5 (d5) and day 11 (d11) consecutively.
Figure 3B:
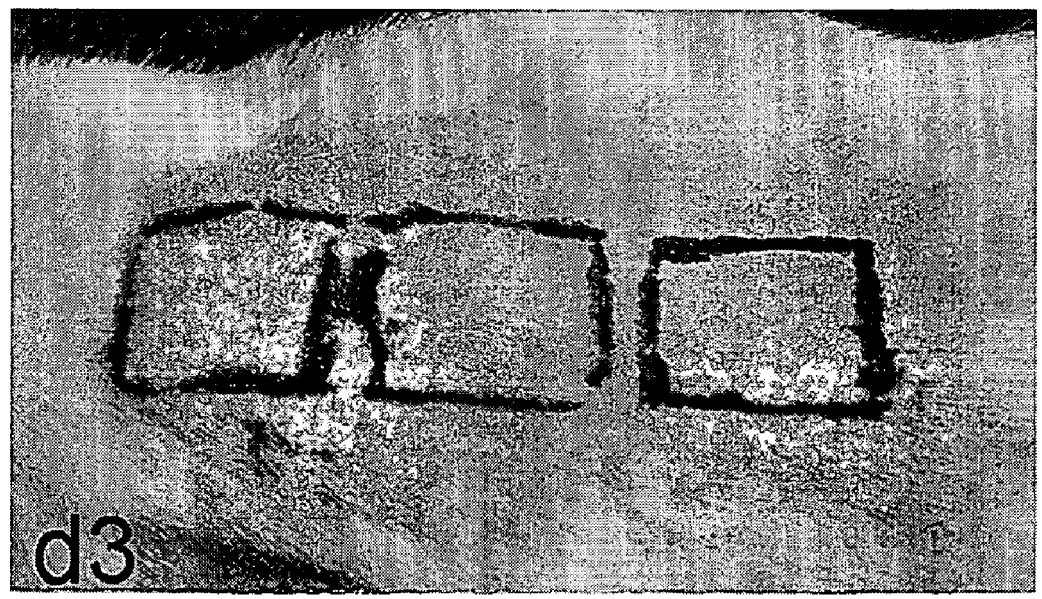
Figure 3C:
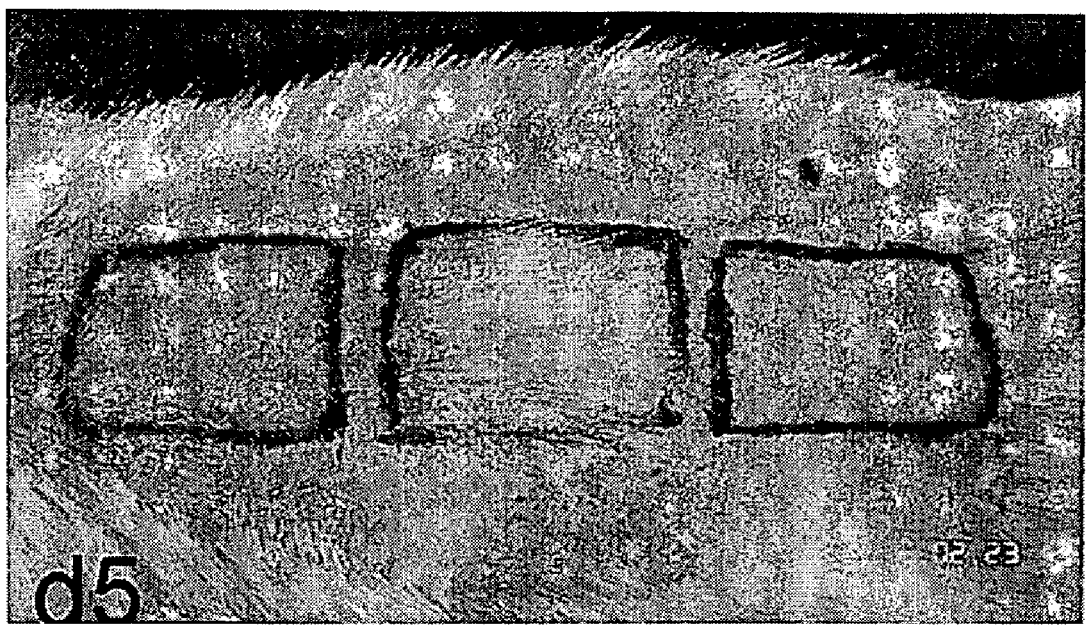
Figure 3D:
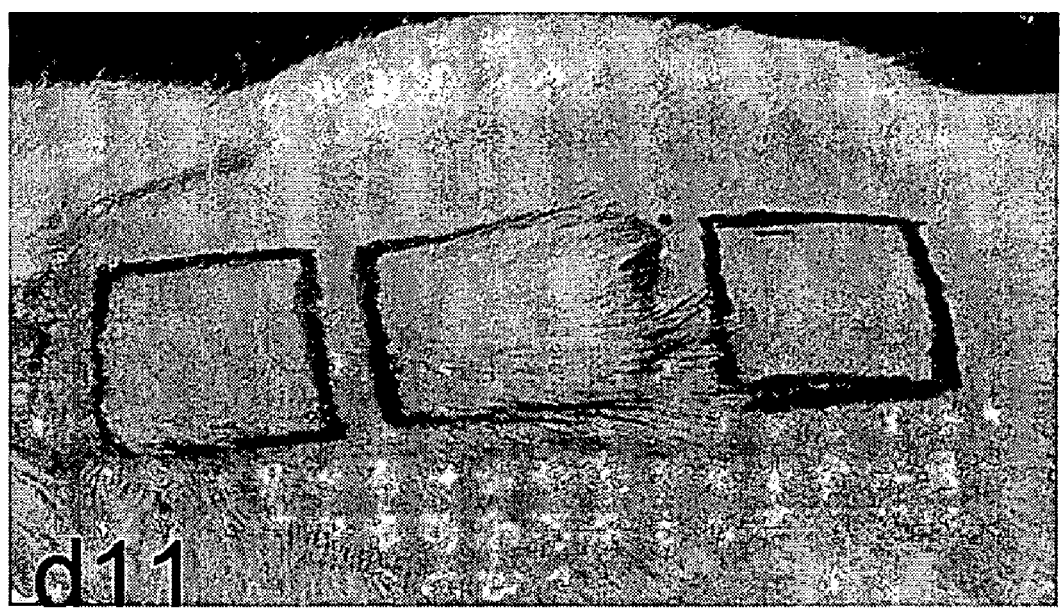

Hematoxylin and Eosin (H&E) staining was performed to microscopically examine the skin area treated with 200 mg/ml of lactoferrin or the control vehicle for 14 days. After 14 days of the treatment, histologic analysis of skin showed a significant number of anagen-phase hair follicles were found in both control vehicle-treated and lactoferrin-treated areas of the skin as indicated by the arrows shown in FIGS. 2A and 2B. As shown in FIG. 2B, the number of anagen phase hair follicles in the lactoferrin-treated area was approximately two-fold greater than those in the area treated with the control vehicle as evident in FIG. 2A. Thus, the proliferation of the anagen phase hair follicles evidently reflected the hair growth observed in the lactoferrin-treated area. However, there was no significant difference in skin thickness between lactoferrin-treated and control vehicle-treated skins. Accordingly, these data showed that administration of an effective amount of lactoferrin resulted in hair growth in the young mice.

Example 2

Use of Lactoferrin to Increase Hair Growth in Aged Mice

To further test whether lactoferrin could induce hair growth in aged mice, five male ICR mice, each 11 months old, were similarly shaved and marked with three areas of the exposed dorsal skin as described in Example 1. The marked areas of the mice were applied by spreading topically on the exposed skin areas 60 μl of aqueous solutions of bovine lactoferrin (100 mg/ml), 60 μl of bovine lactoferrin (200 mg/ml) and 60 μl of control vehicle (water) twice a day. Observation for hair growth in the marked areas was made daily after the first treatment. After 11 days of treatment, prominent hair growth was observed in the skin area treated with 200 mg/ml of lactoferrin, but not with control vehicle alone as shown in FIGS. 3A through 3D. In general, the mice treated with 200 mg/ml of lactoferrin began to grow hair on the treated areas 4-6 days after the treatment. The mice administered with 100 mg/ml lactofferin were found to grow hair on the treated areas 6-8 days after the treatment. Spontaneous hair growth in the control area was only observed 21-23 days after the treatment. The hair growth-promoting effect of lactoferrin was consistently observed in all tested mice.

Figure 4A:
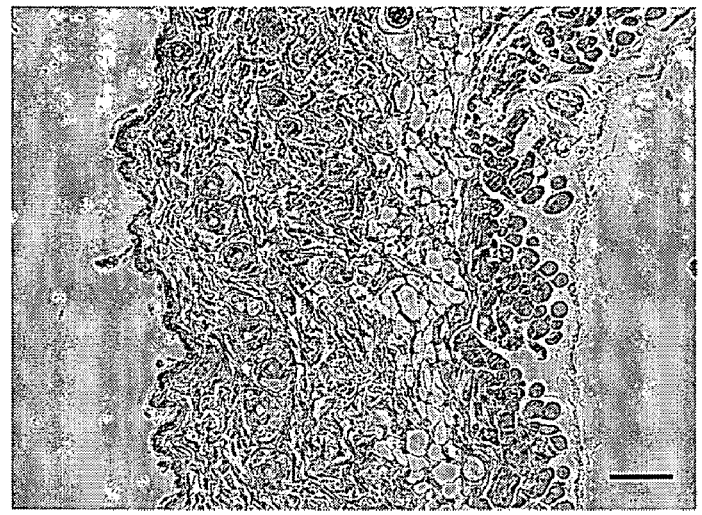
FIG. 4A is a microscopic image showing a histological slide of the skin tissue from the 11-month old ICR mouse treated with a control vehicle (water), where the image has a 100× magnification with a scale bar of 100 μm.
Figure 4B:
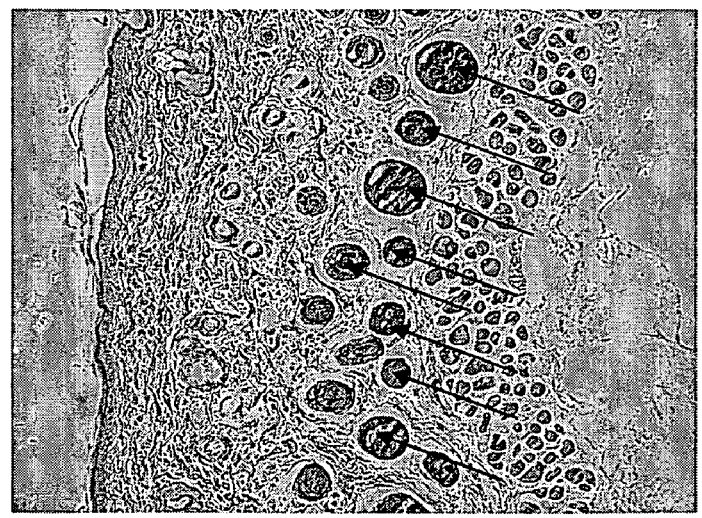
FIG. 4B is a microscopic image showing a histological slide of the skin tissue from the same 11-month old ICR mouse shown in FIG. 4A treated with lactoferrin, the image having the same magnification as FIG. 4A.

The histological examination confirmed the effect of lactoferrin in the activation of hair follicles as shown in FIGS. 4A and 4B. The H&E staining method was performed in a manner similar to Example 1 to examine the skin area treated with 200 mg/ml of lactoferrin or the control vehicle for 14 days. As shown in FIG. 4B, a large number of anagen-phase (actively growing stage) hair follicles (indicated by the arrows) were found in the hypodermis of the lactoferrin-treated area. In contrast, the control area exhibited uniform telogen-phase (resting stage) follicles in the dermis as shown in FIG. 4A. Thus, the hair follicles are clearly activated or triggered to re-enter from the telogen-phase to the anagen-phase. The activation of the hair follicles also reflects the hair growth observed in the lactoferrin-treated area. In addition, increased subcutaneous fat and increased thickness of skin was observed in the lactoferrin-treated area as compared with the control area of the same mice. There were no inflammation and morphological abnormalities found in the skin of the lactoferrin-treated mice. Thus, the results indicated that administration of an effective amount of lactoferrin could dramatically stimulate hair growth in the aged mice.

Example 3

Preparation of Lactoferricin

Lactoferricin is a bioactive peptide fragment (3196 Da) derived from lactoferrin that contains the bactericidal domain. Lactoferricin is an antimicrobial peptide and is usually generated by gastric pepsin cleavage of lactoferrin.

Lactoferricin was generally prepared by cutting lactoferrin with the protein-cutting enzyme pepsin, although other acidic proteases could also be used. Specifically, 5 g of lactoferrin was prepared and mixed with 100 ml of double deionized water ($ddH_2O$) into a commercially obtained bovine lactoferrin solution. The solution was then adjusted with 1M of hydrochloric acid (HCl) to yield a pH value of 2.5. Next, 30 mg of pepsin A powder was dissolved in the solution and an enzyme reaction that cuts lactoferrin into lactoferricin was allowed to proceed at 37° C. for at least 4 hours. The reaction was stopped by heating the solution in a hot water bath at 80° C. for another 15 minutes before cooling at room temperature. The solution was neutralized using 1M of NaOH and spun down at high speed centrifugation (17000 rpm at 4° C.) for 15 minutes. The supernatant separated from the centrifugation was collected to yield lactoferricin. Lactoferricin obtained as described above may be blended with other ingredients to form the composition that promotes hair growth in the subsequent method.

Example 4

Figure 5:
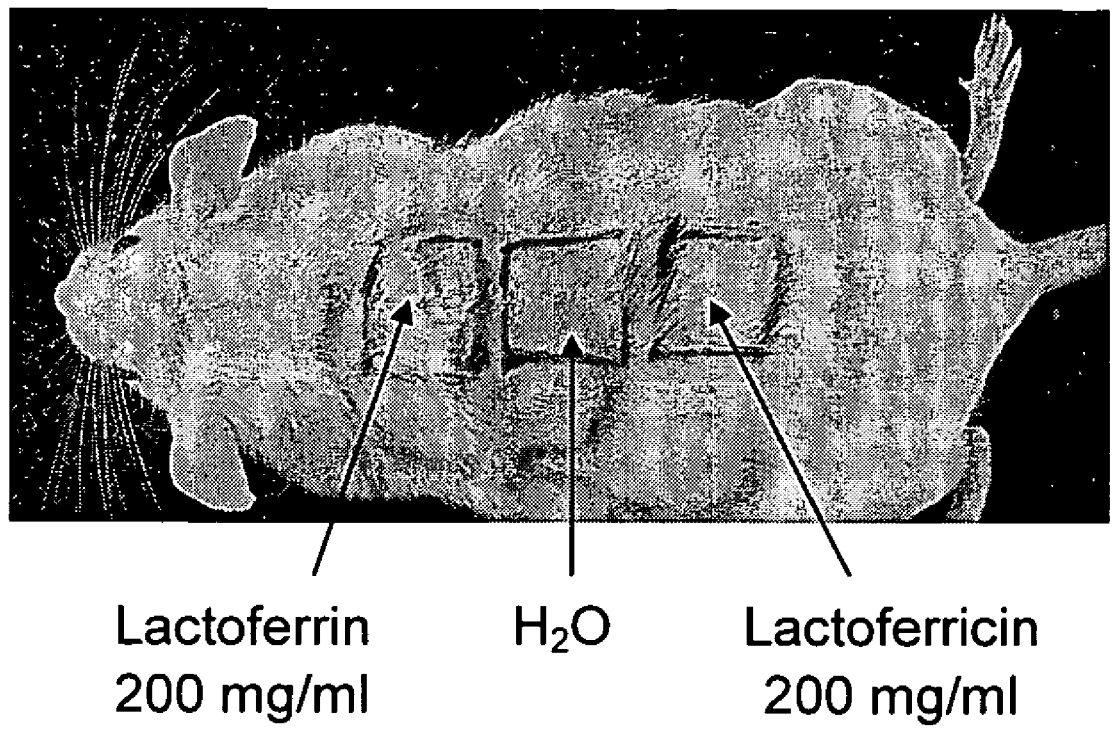
FIG. 5 is a macroscopic image showing a top view of a 4-month old female ICR mouse with a patch of shaved dorsal skin subjected to three different treatments in the marked regions.

Use of Lactoferrin and Lactoferricin to Increase Hair Growth in 4-Month Old Female Mice The hair growth effect was also studied using 2 female mice, each 4 months old, shaved and marked with three areas of the exposed dorsal skin as described in Example 1, but as indicated in FIG. 5, showing one such mouse. The marked areas of the mice were applied by spreading topically on the exposed skin areas 60 μl of aqueous solutions of bovine lactoferrin (200 mg/ml), 60 μl of control vehicle (water), and 60 μl of bovine lactoferricin, obtained as set forth in Example 3, (200 mg/ml) twice daily. Observation for hair growth in the marked areas is made daily after the first treatment. After 10 days of treatment, prominent hair growth was observed in the skin area treated with 200 mg/ml of lactoferrin and 200 mg/ml of lactoferricin, but not with control vehicle alone, as shown in FIG. 5. Also, it was noted that the area treated with 200 mg/ml of lactoferricin showed a greater amount of hair growth as compared with the area treated with lactoferrin of the same amount. The hair growth-promoting effect of lactoferrin or lactoferricin was consistently observed in all tested mice. Although lactoferricin was prepared by the method described in Example 3 above, the present invention should not be limited to use only lactoferricin prepared in such manner. Lactoferricin prepared by other methods would still fall within the scope of the present invention.

Therefore, the present invention provides a method for promoting hair growth which is effective for animals regardless of their gender or age. After the animal was treated with a composition comprising an effective amount of lactoferrin or lactoferricin, hair growth was observed on the treated skin area of the mouse. Furthermore, it is understood by one skilled in the art in view of the present disclosure that lactoferricin and other derivatives or analogs of lactoferrin may also be used in the method of the present invention to promote hair growth for the animal suffering from hair loss, whether due to a disease or as a natural cause.

Summarizing from the above disclosure, the present invention provides a novel use of lactoferrin for promoting hair growth in an animal. While lactoferrin is generally recognized as a safe composition by FDA, it has additional benefits of being hypoallergic and non-inflammatory on the tested animals.

Although the embodiments were described with mice as examples to show the novel use of lactoferrin for promoting hair growth, the present invention should not be limited as such. It should be understood by one having an ordinary level of skill in the art in view of the present disclosure that the present method is equivalently applicable to any warm-blooded animals having hair follicles or hair follicle epithelial cells for growing hair, including humans, commercially relevant mammals such as cattle, pigs, horses, sheep, cats, dogs, mice, rats, rabbits, and pets, birds including commercially relevant birds such as chickens, ducks, geese, and turkeys. The present invention shall not be limited to using bovine lactoferrin only, since other sources of lactoferrin acquired without ethical issues may also be used in the present invention.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method for promoting hair growth, comprising administering to a subject in need thereof a composition containing an effective amount of lactoferrin or lactoferricin, wherein the lactoferrin or lactoferricin is the only active ingredient in the composition.

2. The method according to claim 1, wherein the composition is administered to a skin area where promoting hair growth is needed by spread, spray, steam, or injection.

3. The method according to claim 1, wherein the administering step is performed by soaking or bathing the subject in the composition.

4. The method according to claim 1, wherein the composition is administered topically to a skin area where promoting hair growth is needed.

5. The method according to claim 1, wherein the composition contains about 50 mg/ml to about 500 mg/ml of the lactoferrin or lactoferricin.

6. The method according to claim 5, wherein the composition contains about 100 mg/ml to about 250 mg/ml of the lactoferrin or lactoferricin.

7. The method according to claim 6, wherein the composition contains about 200 mg/ml of the lactoferrin or lactoferricin.

8. The method according to claim 1, wherein the lactoferrin or lactoferricin is bovine lactoferrin or bovine lactoferricin.

9. The method according to claim 1, wherein the composition is formulated in a form selected from the group consisting of an ointment, a shampoo, a conditioner, a lotion, a tonic, a gel, and a mousse.

10. The method according to claim 1, wherein the composition further contains a pharmaceutically acceptable carrier.

11. The method according to claim 1, wherein the subject is a human.

* * * * *